United States Patent
Chun

(10) Patent No.: US 6,238,707 B1
(45) Date of Patent: May 29, 2001

(54) HERBAL HORMONE BALANCE COMPOSITION

(76) Inventor: Zhang Chun, 1665 E. Fourth St., #109, Santa Ana, CA (US) 92701

( * ) Notice: Subject to any disclaimer, the term of this patent is extended or adjusted under 35 U.S.C. 154(b) by 0 days.

(21) Appl. No.: 09/686,828

(22) Filed: Oct. 11, 2000

(51) Int. Cl.[7] .................................................... A61K 35/78
(52) U.S. Cl. .......................... 424/725; 424/734; 424/740; 424/489; 424/498; 424/520; 424/537; 514/899; 514/870
(58) Field of Search .................................. 424/195.1, 489, 424/498, 725, 734, 740; 514/899

(56) References Cited

U.S. PATENT DOCUMENTS 5,874,084 * 2/1999 Yng-Wong .
5,968,518 * 10/1999 Pike .

* cited by examiner

Primary Examiner—Leon B. Lankford, Jr.
Assistant Examiner—Ruth A. Davis

(57) ABSTRACT

The present invention comprises a selection of herbal, organic and inorganic materials with curative effects combined in a powdered form for human ingestion. The demonstrated benefits on human female hormone regulation or replacement include return from irregular to regular and less painful menstrual cycles, raising estrogen and progesterone levels to normal levels through menstrual cycles, return to regular menstrual cycle hormone levels with apparent infertility cure, and return to normative metabolic response from apparent circulatory abnormalities such as excessive sweating, edema, cold hand and feet, stiffness and other such symptoms. The hormone regulation powder comprises motherwort, Epimedium (barrenwort), *Polygonum multiforum* root and stem (fleece flower), millettia stem, *Paeoniae radix* (red Peony root), *Achyranthes bidentata, Albizia julibrissin, Philodendron domesticum, Lycium barbarum,* oyster shell, cow placenta, royal jelly, vitamin E, *Astragalus chinensis* and *Gardenia augusta* or *jasminoides* and further optionally comprises Wolfberry fruit, ginseng, asia bell, chinese angelica root, *Rehmannia glutinosa*, donkey hide gelatin, white peony root, *Poris cocos*, chinese yam or piloce antler.

2 Claims, No Drawings

HERBAL HORMONE BALANCE COMPOSITION

BACKGROUND OF THE INVENTION

The present invention relates to herbal compositions for female human hormone replacement or regulation.

In U.S. Pat. No. 5,942,233, the following functions for *Astragalus* and *Achyranthes bidentata* root are disclosed: "Herbal composition for stimulating blood circulation In order to completely remove toxin from human body, the inventor has studied intensively and the herbs as follows were screened: safflowers (*Crocus sativus*), rhubarb (*Rheum officinale*), red sage root (*Salvia multiorrhiza*), ligusticum (*Cnidium officinale*), Momordica cochinchinensis, achyrantlies root (*Achyranthes bidentata*), and astragalus root (*Astragalus hiroshinianus*). When they are added to the herb composition of the invention, the amount used is about 20% to about 60% by weight based on the total weight of the herb composition. As to the individual effect of these toxin removing herbal materials, for example, astragalus root can invigorate vital energy and replenish "yang", relieve exterior syndrome, induce dieresis to alleviate edema, and remove the pus. In addition, it has dual regulatory effects to blood pressure, that is, decreasing blood pressure for hypertension and increasing blood pressure for hypertension."

*Lycium chinense* (Cortex of Wolfberry root) and *Gardenia jasminoides* have been found to be of importance as a component of an herbal composition in U.S. Pat. No. 5,874,084 for hot flashes (intense heat sensation, flushing, profuse sweating, palpitations, and/or sense of anxiety) stating that such occurrences for a menopausal woman may be substantially eliminated or ameliorated by administering to a woman in need of treatment an effective amount of ingestible material which has as substantially the only active ingredient a herbal complex.

Motherwort is described as a component in a topical paste in U.S. Pat. No. 5,968,518 comprising as active ingredients chickweed, yarrow, wormwood, motherwort, pennyroyal, and dandelion in a vehicle of olive-oil and beeswax.

In U.S. Pat. No. 5,466,452, *Radix paeoniae* (peony root) is disclosed as a substantial component in a topical treatment for skin inflammations.

*Polygonum multiflorum* can have the effect of lowering blood glucose as in U.S. Pat. No. 5,531,991. A composition and method for treating hyperglycemia which utilize an extract of the Chinese herb *Polygonum multiflorum*. The herb is extracted with 0.1N $NH_4OH$ and centrifuged. The supernatant is applied to a Sephadex G-25 column. Three fractions are collected. The fractions exhibit a high insulin potentiating activity in fat cell assays and are shown to lower blood glucose levels.

Albizia has been shown to comprise physiologic effects related to the human nervous system as in U.S. Pat. No. 5,688,938, as follows: "The results obtained with budmunchiamine A illustrate the predictive power of the structure-activity studies and the novel structural information to be gained by testing natural products. One of the structural variations on the polyamine motif that seems to increase potency is the presence of the cyclic version of the straight-chain parent molecule. Budmunchiamine A, isolated from the plant *Albizia amara*, is a cyclic derivative of spermine (FIG. 1a). The addition of budmunchiamine A to bovine parathyroid cells caused a rapid and transient increase in $>Ca^{2+}!_i$ that persisted in the absence of extracellular $Ca^{2+}$ and was blunted by pretreatment with PMA. It therefore causes the mobilization of intracellular $Ca^{2+}$ in parathyroid cells, probably by acting on the calcium receptor. It is about equipotent with spermine ($EC_{50}$ about 200 .mu.M), yet carries one less positive charge (+3) than does spermine."

The effectiveness of cow placenta and a method of preparation for biologically effective portions thereof are described in U.S. Pat. No. 4,169,139 as follows:

"It is another object of the invention to provide a method of producing biologically active mucoprotide material from mammalian liver and the like which results in higher yields than methods used heretofore as well as minimization of bacterial contamination resulting in pyrogenicity which gives a non-usable clinical product.

"The above and other objects of the invention will be apparent from the ensuing description and the appended claims.

"We have found that much more consistently active products at higher yields and having enhanced stability result from a procedure described below.

"Mammalian liver, placenta, spleen, kidney, pancreas, and pituitary glands are some of the preferred sources of these biologically-active mucoprotides. Liver and placenta are preferred. However, tests indicate their presence in significant amounts in all types of mammalian tissue. The source material should come from healthy animals and should be treated mechanically to remove extraneous fat, fibrous material, and the like, leaving primarily the tissue characteristic of the organ, for example, parenchyma in the case of liver."

It is known that as a topical application, royal jelly has certain antimicrobial properties.

SUMMARY OF THE INVENTION

The present invention comprises a selection of herbal, organic and inorganic materials with curative effects combined in a powdered form for human ingestion. The demonstrated benefits on human female hormone regulation or replacement include return from irregular to regular and less painful menstrual cycles, raising estrogen and progesterone levels to normal levels through menstrual cycles, return to regular menstrual cycle hormone levels with apparent infertility cure, and return to normative metabolic response from apparent circulatory abnormalities such as excessive sweating, edema, cold hand and feet, stiffness and other such symptoms.

DETAILED DESCRIPTION OF THE INVENTION

The following is a list of components and approximate weight percents for each essential component in the invention composition:

| Component Name | Weight Percent |
| --- | --- |
| Motherwort (dried) | 3.0–5.0% |
| Epidemium (barrenwort, family Berberidacae in dried form) | 3.0–5.0% |
| Fleece-flower root (Polygonum multiflorum root) | 5.0–10.0% |
| Ji Xue Teng (milletia stem) | 5.0–8.0% |
| Ye Jiao Teng (Polygonum multiflorum stem) | 5.0–8.0% |
| Red Peony Root (Paeoniae radix) | 5.0–8.0% |
| Niu Xi (Achyranthes bidentata) | 5.0–10.0% |

-continued

| Component Name | Weight Percent |
| --- | --- |
| He Huan Pi (Albizia julibrissin) | 5.0–8.0% |
| Philodendron (Philodendron domesticum) | 5.0–8.0% |
| Di Gu Pi (Lycium barbarum) | 5.0–8.0% |
| Oyster Shell (Pteriae concha) | 5.0–8.0% |
| Cow Placenta (dried power) | 0.5–1.0% |
| Royal Jelly | 1.0–3.0% |
| Vitamin E | 1.0–3.0% |
| Sha Yuan Zi (Astragalus chinensis) | 5.0–10.0% |
| Mian Si Zi (Gardenia augusta or jasminoie) | 5.0–10.0% |
| Total | 63.5–100.0 |

The following are optionally added to the invention composition for their beneficial effects:

| Component Name | Weight Percent |
| --- | --- |
| Wolfberry Fruit (dried cortex) | 5.0–10.0% |
| Ginseng | 3.0–5.0% |
| Asia Bell | 3.0–5.0% |
| Chinese Angelica Root | 5.0–8.0% |
| Rehmannia Glutinosa | 5.0–10.0% |
| Donkey Hide Gelation | 5.0–8.0% |
| White Peony Root | 5.0–8.0% |
| Poris Cocos | 5.0–8.0% |
| Chinese Yam | 5.0–8.0% |
| Plioce Antler | 5.0–8.0% |

It will be appreciated to those skilled in this art that the above approximate weight percents are dependent on generally expected potencies of the components, whereby the relative weight percents will vary sometimes substantially from the above individual amounts. It will be within the skilled person's knowledge with this disclosure that the objects of the present invention require the inclusion of each of the components in relative approximate weight percents above. As disclosed in the prior art, individual components comprise medicinal effects on the human female endocrine and circulator system and further comprise substantially absorbable molecular classes. Subgroups within the above list comprise those components which have similar known effects, i.e., some components have been shown to have substantial effects while administration of others in combination comprise ineffective or adverse effects.

The above components are ground to a powder form well known in the Chinese herbal art. Such grinding may be accomplished manually with the components separately ground or ground together. The powder mixture is preferably substantially finer than 100 mesh. Each of the components in the above ranges is required to obtain the objects of the present invention.

The powder of the above composition is formed into capsules or pills for convenient ingestion. Treatment to achieve the objects of using the invention composition is preferably from 1 to 12 months, more preferably from 1 to 6 months, and most preferably from 2 to 3 months. Daily ingestion at morning, midday and evening times is preferred.

Dosage for effective treatment for irregular or painful menstruation or the above described circulatory problems is about 475 to 750 milligrams three times per day. Dosage for effective treatment for menopause conditions and related disabilities is about 950 to 1500 milligrams three times per day. Capsule or pill forms of the invention composition are conveniently made in about 750 milligrams.

The following examples are case reports from patients undergoing a course of treatment and the results therefore:

Case 1:
Patient data: Female, age 46
Length of Treatment: 6 months
Daily dosage: 4500 milligrams per day, in 3 doses.
Pre-treatment condition: Difficult menopausal syndrome with frequent hot flashes in combination with very low measured levels of estrogen and progesterone.
Treatment results: The patient's treating physician measured estrogen and progesterone levels after treatment to find they had risen to within normal range at the end of the treatment. Menopausal symptoms reduced in severity and frequency.

Case 2:
Patient data: Female, age 30
Length of Treatment: 6 months
Daily dosage: 4500 milligrams per day, in 3 doses.
Pre-treatment condition: Infertility over two year period. Irregular menstrual cycles in that time period.
Treatment results: Apparently effective since subject became pregnant at the end of the treatment time period and gave birth to a boy as a result.

Case 3:
Patient data: Female, age 44
Length of Treatment: 6 months
Daily dosage: 4500 milligrams per day, in 3 doses.
Pre-treatment condition: History over at least two years of irregular menstrual cycles and severe sweating during menstruation under moderate ambient conditions.
Treatment results: Normal monthly menstrual cycles observed at least 3 months in follow-up after treatment. Normal response to ambient temperature has returned without excessive sweating.

Case 4:
Patient data: Female, age 45
Length of Treatment: 3 months
Daily dosage: 1500 milligrams per day, in 3 doses.
Pre-treatment condition: History over seven years of severe coldness and lack of adequate circulation in hands and feet. Subject exhibited moderate to severe depression from chronic joint ague and tension over condition.
Treatment results: No noticeable coldness in the hands or feet with resulting improvement in mental attitude. Apparently improved psychological response to normal life challenges.

Case 5:
Patient data: Female, age 42
Length of Treatment: 2 months
Daily dosage: 1500 milligrams per day, in 3 doses.
Pre-treatment condition: History over five years of moderate to severe joint pain in ankles, with inability to run at all.
Treatment results: Joint pain at the end of treatment and over some months thereafter in follow-up has reduced to unnoticeable levels. Stiffness and aching have disappeared and she is able to run for a substantial distance.

Case 6:
Patient data: Female, age 30
Length of Treatment: 1 month/3 months

Daily dosage: 1500 milligrams per day, in 3 doses.

Pre-treatment condition: History over three years of moderate to severe headaches especially at the time of menstruation. Exhausted and tired most of the time and unable to live a desired level of activity.

Treatment results: At 1 month, the exhaustion was relieved with most headache symptoms alleviated. At 3 months, all headache symptoms disappeared.

Case 7:

Patient data: Female, age 73

Length of Treatment: 3 months

Daily dosage: 1500 milligrams per day, in 3 doses.

Pre-treatment condition: History over ten years of moderate to severe joint pain and associated thirst and frequent micturition at night with resulting insomnia. The chronic pain and insomnia resulted in negative responsiveness and difficulty in interpersonal relations.

Treatment results: Joint pain at the end of treatment and over some months thereafter in follow-up has reduced to unnoticeable levels. Thirst and frequent urination have been reduced to normal levels, the beneficial effects of this treatment of course permitting normal night's sleep.

The above cases demonstrate the beneficial effects of the invention composition. The number of components in the composition and their interaction after partial digestion and lumen absorption into the bloodstream makes organ and tissue level responses to specific molecular events very difficult. That there are a wide range of beneficial effects are most effectively considered in light of the rather universal effects of the endocrine system on the female human. Medical science is not capable to defining all the effects of the individual hormones on all tissues in combination with the several opposing and complementary hormones and their enzyme activators. The present inventor has discovered a complex mixture of molecules that produce a spectrum of benefits not predictable from cosideration of the benefits of the several components separate from the composition. The present composition ingested by the human female results in some positive response without side effects after administration to hundreds of subjects.

The above composition and methods present the skilled person with considerable and wide ranges from which to choose appropriate obvious modifications for the above examples. However, the objects of the present invention will still be obtained by the skilled person applying such disclosures in an appropriate manner.

I claim:

1. A human female hormone regulation powder comprising, according to the following list by approximate weight percents:

Motherwort (dried) at about 3.0–5.0%;
Epimedium (barrenwort, family Berberidacae in dried form) at about 3.0–5.0%;
Fleece-flower root (*Polygonum multiflorum* root) at about 5.0–10.0%;
Ji Xue Teng (MILLETIA stem) at about 5.0–8.0%;
Ye Jiao Teng (*Polygonum multiflorum* stem) at about 5.0–8.0%;
Red Peony Root (*Paeoniae radix*) at about 5.0–8.0%;
Niu Xi (*Achyranthes bidentata*) at about 5.0–10.0%;
He Huan Pi (*Albizia julibrissin*) at about 5.0–8.0%;
Philodendron (*Philodendron domesticum*) at about 5.0–8.0%;
Di Gu Pi (*Lycium barbarum*) at about 5.0–8.0%;
Oyster Shell (*Pteriae concha*) at about 5.0–8.0%;
Cow Placenta (dried powder) at about 0.5–1.0%;
Royal Jelly at about 1.0–3.0%;
Vitamin E at about 1.0–3.0%;
Sha Yuan Zi (*Astragalus chinensis*) at about 5.0–10.0%; and
Mian Si Zi (*Gardenia augusta* or JASMINOIDES) at about 5.0–10.0%.

2. The powder of claim 1 wherein optional additional components are selected from among the group consisting of Wolfberry Fruit (dried cortex), Ginseng, Asia Bell, Chinese Angelica Root, Rehmannia Glutinosa, Donkey Hide Gelation, White Peony Root, Poris Cocos, Chinese Yam, and Piloce Antler.

* * * * *